United States Patent
Soper et al.

(10) Patent No.: US 10,544,073 B2
(45) Date of Patent: Jan. 28, 2020

(54) PROCESSES FOR PRODUCING PROPYLENE GLYCOL

(71) Applicant: ARCHER DANIELS MIDLAND COMPANY, Decatur, IL (US)

(72) Inventors: John G Soper, Mt. Zion, IL (US); Joshua Terrian, Lovington, IL (US)

(73) Assignee: ARCHER DANIELS MIDLAND COMPANY, Decatur, IL (US)

(*) Notice: Subject to any disclaimer, the term of this patent is extended or adjusted under 35 U.S.C. 154(b) by 0 days.

(21) Appl. No.: 15/105,795

(22) PCT Filed: Dec. 9, 2014

(86) PCT No.: PCT/US2014/069274
§ 371 (c)(1),
(2) Date: Jun. 17, 2016

(87) PCT Pub. No.: WO2015/100003
PCT Pub. Date: Jul. 2, 2015

(65) Prior Publication Data
US 2016/0311742 A1  Oct. 27, 2016

Related U.S. Application Data

(60) Provisional application No. 61/920,131, filed on Dec. 23, 2013.

(51) Int. Cl.
  C07C 29/60  (2006.01)
  C07C 29/76  (2006.01)
(52) U.S. Cl.
  CPC .............. *C07C 29/60* (2013.01); *C07C 29/76* (2013.01)

(58) Field of Classification Search
  CPC .................................................... C07C 29/60
  See application file for complete search history.

(56) References Cited

U.S. PATENT DOCUMENTS

| 3,481,836 | A | 12/1969 | Nomura et al. |
|---|---|---|---|
| 4,338,472 | A | 7/1982 | Sirkar et al. |
| 7,790,937 | B2 | 9/2010 | Henkelmann et al. |
| 2010/0240934 | A1 | 9/2010 | Henkelmann et al. |
| 2010/0312024 | A1 | 12/2010 | Henkelmann et al. |
| 2011/0112335 | A1* | 5/2011 | Godavarthy ............ C07C 29/60 568/861 |
| 2011/0207971 | A1 | 8/2011 | Frye et al. |

OTHER PUBLICATIONS

Blaine R. Copenheaver, ISR and Written Opinion, dated Feb. 4, 2015, pp. 1-14, USA.

* cited by examiner

*Primary Examiner* — Ana Z Muresan
(74) *Attorney, Agent, or Firm* — Andrew F. Nilles

(57) ABSTRACT

Processes for producing propylene glycol are disclosed. The processes may comprise subjecting a polyol to a hydrogenolysis reaction, thus producing propylene glycol and a product stream including an unreacted polyol and at least one unwanted compound. The process may include subjecting the product stream to a process that removes at least a portion of the at least one unwanted compound, thus producing a cleaned product stream, and subjecting the cleaned product stream to the hydrogenolysis reaction. Systems for implementing such processes are also described.

11 Claims, 3 Drawing Sheets

SUMMARY OF PILOT SCALE ION-EXCLUSION C-SEP FOR SALT REDUCTION OF GLYCEROL RECOVERY COLUMN (GRC) BOTTOMS

| | <---Mitsubishi UBK 555 Na+form resin---> | | | | | | <---Dowex 99 320 Resin---> | | | | | | | | | | | | | |
|---|---|---|---|---|---|---|---|---|---|---|---|---|---|---|---|---|---|---|---|---|
| | A-1 | B-2 | C-1 | E-2 | E-3 | G-2 | M-1 | N-0 | N-7 | N-8 | N-12 | N-14 | N-19 | N-21 | N-22 | N-23 | N-24 | N-25 | N-28 | N-29 | O-9 |
| STEP TIME (MIN) | 11 | 11 | 11 | 11 | 11 | 11 | 11 | 6.0 | 5.0 | 5.5 | 5.0 | 5.0 | 5.0 | 5.0 | 5.0 | 5.0 | 5.0 | 5.0 | 5.0 | 5.0 | 5.0 |
| TOTAL RUN TIME (MIN) | 1020 | 900 | 1440 | 1440 | 990 | 2370 | 816 | 75 | 60 | 66 | 30 | 60 | 60 | 60 | 60 | 60 | 60 | 60 | 60 | 60 | 990 |
| SODIUM REDUCTION, % | 87.2 | 85.6 | 81.9 | 97.4 | 92.5 | 72.6 | 70.4 | 82.7 | 94.9 | 96.8 | 95.5 | 88.2 | 96.9 | 98.6 | 99.6 | 99.5 | 99.6 | 99.6 | 99.3 | 99.6 | 94.8 |
| GLYCEROL YIELD, % | 93.7 | 86.8 | 90.6 | 87.6 | 86.3 | 98.7 | 93.1 | 53.3 | 96.4 | 90.0 | 98.3 | 99.3 | 94.9 | 88.6 | 98.7 | 98.2 | 98.8 | 97.6 | 95.4 | 93.0 | 98.8 |
| ACTUAL FLOWS | | | | | | | | | | | | | | | | | | | | | |
| FEED | 4.7 | 7.2 | 5.3 | 2.4 | 6.9 | 6.5 | 4.9 | 8.0 | 7.9 | 8.5 | 8.0 | 8.2 | 7.9 | 7.1 | 4.2 | 6.3 | 6.7 | 6.7 | 6.9 | 7.0 | 6.6 |
| ENRICHMENT | 13.7 | 11.6 | 11.2 | 13.4 | 11.0 | 11.4 | 4.2 | 27.0 | 27.5 | 25.5 | 27.6 | 24.7 | 28.1 | 34.3 | 36.8 | 25.1 | 26.0 | 29.3 | 30.6 | 27.6 | 29.7 |
| ELUTION | 16.7 | 12.6 | 9.2 | 12.0 | 10.9 | 12.9 | 14.6 | 29.3 | 31.1 | 31.0 | 33.3 | 30.4 | 31.7 | 36.7 | 37.5 | 25.0 | 30.0 | 33.3 | 33.3 | 30.0 | 34.7 |
| RELOAD | 11.0 | 11.0 | 11.0 | 11.0 | 11.0 | 11.0 | 0.0 | 9.3 | 9.3 | 9.3 | 9.3 | 9.3 | 9.3 | 9.3 | 9.3 | 9.3 | 9.3 | 9.3 | 9.3 | 9.3 | 9.3 |
| PRODUCT | 13.9 | 12.0 | 9.0 | 9.7 | 10.9 | 12.5 | 10.4 | 11.7 | 12.9 | 14.8 | 15.0 | 15.0 | 12.9 | 11.7 | 10.0 | 9.2 | 13.3 | 13.3 | 12.1 | 11.7 | 14.3 |
| RAFFINATE | 6.7 | 6.9 | 5.1 | 4.3 | 6.3 | 6.0 | 8.3 | 24.0 | 26.7 | 25.4 | 26.7 | 23.3 | 26.7 | 28.2 | 22.5 | 25.0 | 23.3 | 25.8 | 28.3 | 25.8 | 26.1 |

[ ] BEST RESULTS - Optimal Flow Conditions

FIG. 2

PROCESSES FOR PRODUCING PROPYLENE GLYCOL

CROSS-REFERENCE TO RELATED APPLICATIONS

This application is a national stage entry of International Application No. PCT/US2014/069274, filed Dec. 9, 2014, which itself claims priority to U.S. Provisional Patent Application No. 61/920,131, filed Dec. 23, 2013, each of the contents of the entirety of which are incorporated by this reference.

TECHNICAL FIELD

The present invention relates generally to processes for producing propylene glycol, ethylene glycol, or combinations thereof. More particularly, the present invention relates to processes for improving the production of propylene glycol, ethylene glycol, or combinations thereof in a hydrogenolysis reaction by re-using and/or cleaning a by-product stream of the hydrogenolysis reaction after removal of un-wanted compounds from the by-product stream.

BACKGROUND OF THE INVENTION

Polyols are converted to propylene glycol and/or ethylene glycol through a hydrogenolysis reaction. In such reaction, the polyols are converted through a catalytic operation to the desired propylene glycol and/or ethylene glycol. However, during such catalytic operation, other products and/or streams are generated during the reaction such as water, mixed alcohols, mixed diols, other impurities, and unconverted polyols used as the starting material.

These other products and/or streams may be purified, treated, and/or discarded. However, the presence of various un-wanted compounds in such streams may make discarding such streams problematic. Alternatively, the presence of un-reacted polyols or other polyols in a discarded stream may decrease the overall yield of the desired propylene glycol and/or ethylene glycol and make the process less efficient.

Thus, needs exist for processes to eliminate the presence of any un-wanted compounds in such streams and/or processes to recover any un-reacted polyols or other polyols from such streams such that the un-reacted polyols or other polyols may be converted to the desired propylene glycol and/or ethylene glycol, thus, increasing the efficiency of the overall process.

SUMMARY OF THE INVENTION

In each of its various embodiments, the present invention fulfills these needs and discloses processes for removing un-wanted compounds and/or processes for recovering any un-reacted polyols or other polyols from streams or by-products produced in a process for producing propylene glycol and/or ethylene glycol.

In one embodiment, a process for producing propylene glycol comprises subjecting a polyol to a hydrogenolysis reaction, thus producing propylene glycol and a product stream including an unreacted polyol and at least one unwanted compound. The process also includes subjecting the product stream to a process that removes at least a portion of the at least one unwanted compound, thus producing a cleaned product stream, and subjected the cleaned product stream to the hydrogenolysis reaction.

In another embodiment, a process of producing propylene glycol includes subjecting glycerol to a hydrogenolysis reaction, thus producing propylene glycol and a product stream including unreacted glycerol and a sodium salt. The process also includes subjecting the product stream to a process that removes at least a portion of the sodium salt, thus producing a cleaned product stream, and further includes subjecting the cleaned product steam to the hydrogenolysis reaction.

In an additional embodiment, a system for producing propylene glycol includes glycerol, means for converting the glycerol into propylene glycol, a product stream comprising unreacted glycerol and a salt, means for removing at least a portion of the salt from the product stream, a cleaned product stream including the unreacted glycerol and a reduced amount of the salt, and a conduit for placing the cleaned product stream in contact with the glycerol, the means for converting the glycerol into the propylene glycol, or a combination thereof.

DESCRIPTION OF THE DRAWINGS

FIG. 2 illustrates one embodiment of chromatographic separation used in the process for producing enhanced purity glycerin of the present invention.

DETAILED DESCRIPTION OF THE INVENTION

Figure 1:
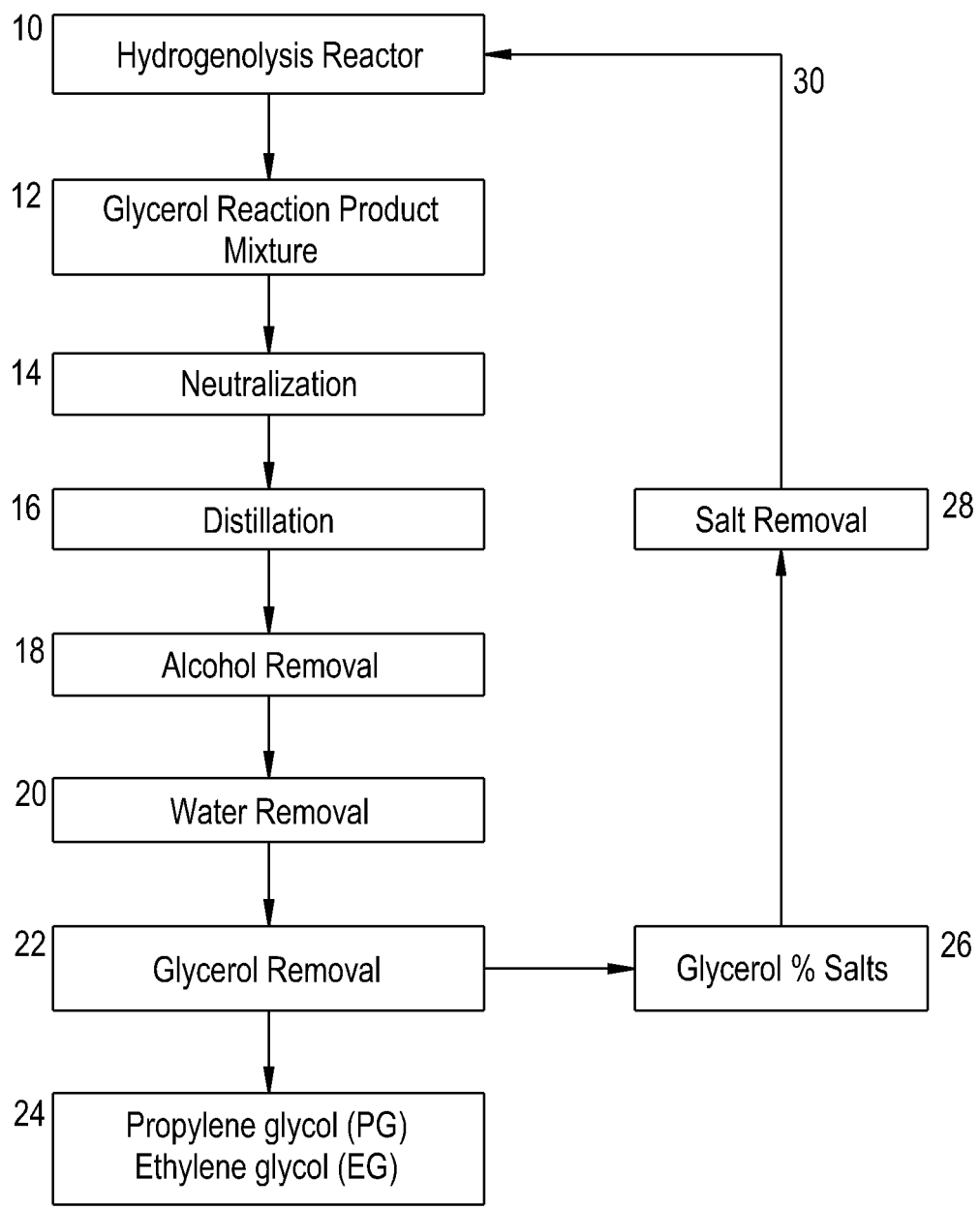
FIG. 1 shows one embodiment of a flowchart of a process for producing propylene glycol of the present invention.

Work on the production of propylene glycol and/or ethylene glycol has continued.

In an embodiment, a process for producing propylene glycol comprises subjecting a polyol to a hydrogenolysis reaction, thus producing propylene glycol and a product stream including an unreacted polyol and at least one unwanted compound. The process also includes subjecting the product stream to a process that removes at least a portion of the at least one unwanted compound, thus producing a cleaned product stream, and subjecting the cleaned product stream to the hydrogenolysis reaction.

The product stream may also include other compounds such as unreacted polyol, chains of the polyol (i.e., dimers, trimers, etc . . . of the polyol), or other products. In such embodiments, by placing the cleaned product stream back in the hydrogenolysis reaction, a portion of the unreacted polyol or a portion of the chains of the polyol may be converted into propylene glycol, thus, increasing the efficiency of the hydrogenolysis reaction. In a further embodiment, the cleaned product stream may be blended with the polyol and subsequently subjected to the hydrogenolysis reaction.

In one embodiment, the process that removes the at least a portion of the at least one unwanted compound may be a chromatographic separation and the chromatographic separation may be ion-exclusion. In another embodiment, the process that removes the at least a portion of the at least one unwanted compound may be a C-SEP separation process.

The polyol may be glycerol in one embodiment, but in other embodiments, the polyol may be a six carbon sugar, a six carbon sugar alcohol, a five carbon sugar, a five carbon sugar alcohol, lactate, lactic acid, other sugar alcohol that is able to form hydrogenolysis, or combinations of any thereof. In embodiments where glycerol is the polyol, the cleaned product stream may comprise glycerol (which may be present at 25-65% by weight), polyglycerol (which may be 0-30% by weight), a sodium salt (which may be present at 15,000-30,000 ppm), and combinations of any thereof The unwanted compound may be a salt such as a sodium salt (e.g., sodium sulfate or sodium lactate) or other compound that may be an unwanted compound in the hydrogenolysis reaction.

In a further embodiment, a process for producing propylene glycol includes subjecting glycerol to a hydrogenolysis reaction, thus producing propylene glycol and a product stream including unreacted glycerol and a sodium salt. The process may also include subjecting the product stream to a process that removes at least a portion of the sodium salt, thus producing a cleaned product stream and subjecting the cleaned product stream to the hydrogenolysis reaction. The product stream may also include polyglycerol.

The process may further include mixing glycerol with the cleaned product stream and subjecting the glycerol mixed with the cleaned product stream to the hydrogenolysis reaction. The cleaned product stream may include glycerol (which may be present at 25-65% by weight), polyglycerol (which may be 0-30% by weight), a sodium salt (which may be present at 15,000-30,000 ppm), and combinations of any thereof.

The process that removes at least a portion of the sodium salt may be a chromatographic separation, such as ion-exclusion. In another embodiment, the process that removes at least a portion of the sodium salt may be a C-SEP separation process.

In an additional embodiment, a system for producing propylene glycol includes glycerol, means for converting the glycerol into propylene glycol, a product stream comprising unreacted glycerol and a salt, means for removing at least a portion of the salt from the product stream, a cleaned product stream including the unreacted glycerol and a reduced amount of the salt, and a conduit for placing the cleaned product stream in contact with the glycerol, the means for converting the glycerol into the propylene glycol, or a combination thereof The means for removing the at least a portion of the salt from the product stream may comprise a chromatographic separation apparatus, which may be a C-SEP apparatus having an adsorption zone, an enrichment zone, a desorption zone, and a reload zone. The means for converting the glycerol into the propylene glycol may comprise a reaction vessel and a catalyst.

FIG. 1 shows a flow chart of a hydrogenolysis reaction generally at 10 used to produce propylene glycol and ethylene glycol. A feedstock which may include water or a nonaqueous solvent is prepared. In this embodiment, the feedstock is includes glycerol 12, but in other embodiments, the feedstock may be a sugar, a sugar alcohol, lactate, or lactic acid. The glycerol 12 is placed in a reaction vessel with a metal-containing solid catalyst for the hydrogenolysis reaction which is a catalytic operation. After the hydrogenolysis reaction, the product mixture includes various compounds such as propylene glycol, ethylene glycol, water, mixed alcohols, mixed diols, other impurities, and unreacted glycerol.

This product mixture is subjected to processing which includes neutralization 14 and a distillation process 16, which may include five steps. Alcohol is removed in the distillation at step 18 and water is removed in the distillation at step 20. Glycerol is removed in the distillation from the product mixture at step 22 and the product mixture is subsequently distilled at step 24 to recover the desired propylene glycol and/or ethylene glycol. Removal of the glycerol from the product mixture results in a waste stream at 26 that typically includes glycerol, polyglycerol (formed during the high temperature of the distillation), salts, and/or other polyols. This waste stream 26 has a high BOD load which may be too high to send to waste treatment.

The present invention uses this waste stream 26 by cleaning and/or sending this waste stream 26 back into the hydrogenolysis reaction 10, thus, increasing the efficiency of the hydrogenolysis reaction 10 by converting any un-reacted glycerol and/or polyglycerol to propylene glycol and/or ethylene glycol. In one embodiment, the salts (and/or other impurities) are removed at step 28 from the waste stream 26, such as by ion-exclusion, and the waste stream 26 with the salts removed is recycled back to the hydrogenolysis reactor feed 10 at arrow 30.

The following exemplary, non-limiting examples are provided to further describe the embodiments presented herein. Those having ordinary skill in the art will appreciate that variations of these Examples are possible within the scope of the invention.

EXAMPLE 1

A chromatographic separation (C-90 C-SEP) was set up with 12 columns of 250 mLs each. The configuration of the separation is shown in FIG. 2. The flow rates of FIG. 2 are exemplary as other flow rates may be used. This example was run at 120-130° F., but other temperatures may be employed. Two resins were used in the Examples which included Mitsubishi UBK 555 and Dowex 99 320, which were each in the sodium form.

The material used in this separation was obtained from a hydrogenolysis reaction used to produce propylene glycol and/or ethylene glycol, such as the glycerol and salts stream 26 from FIG. 1. The material included glycerol, polyglycerol, salts, and other wastes (the material may be referred to herein as GRC glycerol). The GRC glycerol was diluted with deionized water to 70% total solids and vacuum filtered through a 25 micron filter paper.

In this example, the GRC glycerol included 35-36% glycerol, 15-26% polyglycerol (principally diglycerol), and 19,500-23,500 ppm sodium (as sodium sulfate and sodium lactate). Different compositions of diluted GRC glycerol were run through the separation of FIG. 2, with the conditions, resins, and results of a number of exemplary runs shown in the table of FIG. 3.

Figure 3:
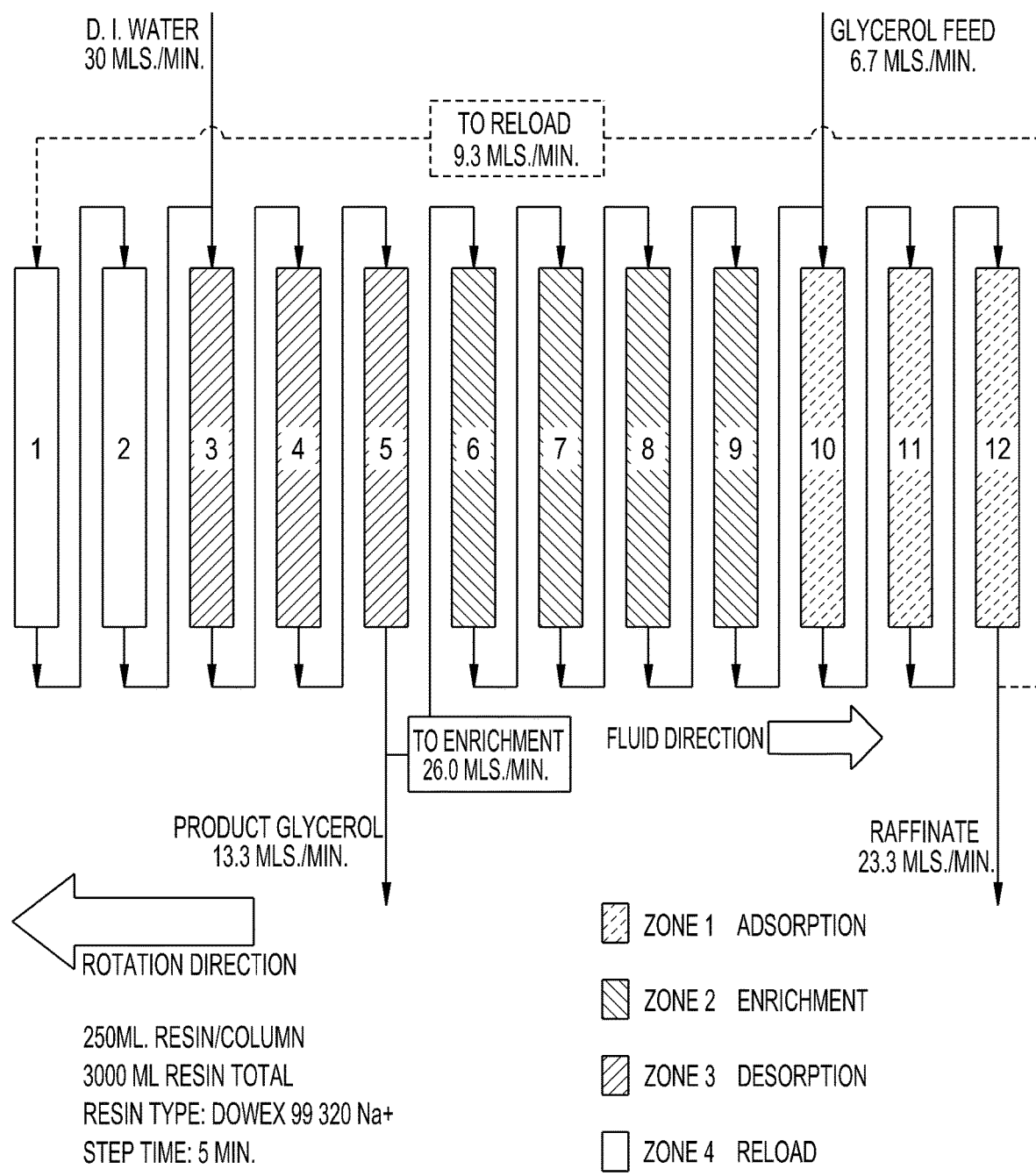
FIG. 3 shows the results of one embodiment of a process for producing propylene glycol of the present invention.

Nine of the exemplary runs of FIG. 3 were further analyzed for polyglycerol material balance. The results of these nine runs, in terms of yield and sodium rejection, are presented in Table 1.

TABLE 1

Glycerol and polyglycerol yield, sodium rejection.

|  | Average | Minimum (%) | Maximum (%) |
| --- | --- | --- | --- |
| Glycerol | 95.5 | 88.6 | 99.3 |
| Polyglycerol | 77.4 | 65.8 | 94.4 |
| Sodium rejection | 97.2 | 91.3 | 99.6 |

EXAMPLE 2

Product obtained from Example 1 was blended with un-reacted glycerol (i.e., USP or virgin glycerol) and water at various ratios and used to feed a 30 cc hydrogenolysis reactor, such as the hydrogenolysis reaction shown in FIG. 1. The catalyst used in this reaction was a commercially available 5% Ni/1% Re/carbon. The reaction conditions were: 205° C. reactor jacket temperature; 1800 psi hydrogen pressure; feed of LHSV=0.7 hr$^{-1}$; hydrogen flow of 1000 cc/min STP; and feed sodium hydroxide concentration of 0.33% by weight. The reactant and product concentrations were determined by a combination of HPLC and GC methods. The results are shown in Table 2. The values are averaged over the time range listed.

TABLE 2

| Time (hr) | % virgin Glycerol | % GRC feed (from Ex. 1) | Conversion % | PG yield Wt. % | PG selectivity Cmol % |
|---|---|---|---|---|---|
| 19-64 | 40 | 0 | 85.85 | 65.85 | 92.84 |
| 88-268 | 38 | 2 | 87.73 | 71.36 | 98.45 |
| 292-996 | 35 | 5 | 85.79 | 76.60 | 108.08 |
| 1014-2052 | 30 | 10 | 82.96 | 86.11 | 125.66 |
| 2099-2285 | 0 | 100 | n.m. | n.m. | n.m. |
| 2309-2449 | 40 | 0 | 85.12 | 66.74 | 94.89 |

The following calculations were used for Table 2: Conversion=(glycerol in product/virgin glycerol in feed); % PG yield=100×(mass PG in product/mass virgin glycerol in feed); wt % PG selectivity=100×(moles carbon in PG product)/(moles carbon in product glycerol); carbon mol %. N.m.=not meaningful-calculations based on virgin glycerol in the feed, which is zero in this instance.

The propylene glycol (PG) yield and selectivity numbers using the feed with the recycled glycerol (i.e., the GRC material from step 30 from FIG. 1) reflect the conversion of some of the glycerol and polyglycerol in the GRC material. The numbers on selectivity are based on the virgin glycerol, thus, the number over 100% indicates that the GRC material is being converted into PG (from glycerol and polyglycerol). From 2099 to 2285 hours, pure GRC feed was used to stress the catalyst and determine what lasting effects (if any) there was from using the GRC feed on catalyst activity. It was unexpectedly found that, as shown in Table 2, the catalyst returned to baseline performance or normal activity levels with pure, virgin glycerol after more than 2000 hours on feed containing the GRC material which indicates no irreversible damage was done to the catalyst.

The GRC material obtained from Example 1 and used in the hydrogenolysis reaction of Example 2 included about 35-36% glycerol, about 15-26% polyglycerol (principally diglycerol), and about 19,500-23,500 ppm sodium.

The present invention has been described with reference to certain exemplary and illustrative embodiments, compositions and uses thereof. However, it will be recognized by persons having ordinary skill in the art that various substitutions, modifications or combinations of any of the exemplary embodiments may be made without departing from the scope of the invention. Thus, the invention is not limited by the description of the exemplary and illustrative embodiments, but rather by the appended claims.

What is claimed is:

1. A process of producing propylene glycol, the process comprising:
    subjecting a polyol to a hydrogenolysis reaction, thus producing propylene glycol and a product stream including an unreacted polyol, polyglycerol and at least one unwanted compound;
    mixing water with the product stream;
    filtering the product stream;
    subjecting the product stream to ion-exclusion chromatography that removes at least a portion of the at least one unwanted compound, thus producing a cleaned product stream;
    blending the cleaned product stream with unreacted polyol; and
    subjecting the cleaned product stream and the unreacted polyol to the hydrogenolysis reaction;
    wherein the cleaned product stream comprises 25-65% glycerol by weight, 0-30% polyglycerol by weight, and 15,000-50,000 ppm sodium.

2. The process according to claim 1, wherein the process that removes the at least a portion of the at least one unwanted compound is a C-SEP separation process.

3. The process according to claim 1, wherein the at least one unwanted compound comprises a salt.

4. The process according to claim 1, wherein the product stream includes unreacted polyol, a chain of the polyol, and a salt.

5. The process according to claim 4, wherein the hydrogenolysis reaction converts at least a portion of the unreacted polyol to the propylene glycol and converts at least a portion of the chain of the polyol to propylene glycol.

6. A process of producing propylene glycol, the process comprising:
    subjecting glycerol to a hydrogenolysis reaction, thus producing propylene glycol and a product stream including unreacted glycerol, polyglycerol and a sodium salt;
    mixing the product stream with water;
    vacuum filtering the product stream
    subjecting the product stream to an ion-exclusion chromatographic separation in a C-SEP separation with a resin in sodium form at a temperature of 120-130° F. that removes at least a portion of the sodium salt, thus producing a cleaned product stream; and
    subjecting the cleaned product steam to the hydrogenolysis reaction.

7. The process of claim 6, further comprising:
    mixing glycerol with the cleaned product stream; and
    subjecting the glycerol mixed with the cleaned product stream to the hydrogenolysis reaction.

8. The process according to claim 6, wherein the cleaned product stream comprises 25-65% glycerol by weight, 0-30% polyglycerol by weight, 15,000-50,000 ppm sodium, or combinations of any thereof.

9. The process according to claim 1, wherein the filtering removes particles 25 microns or larger.

10. The process according to claim 1, wherein the ion-exclusion chromatography occurs at a temperature of from 120-130° F.

11. The process according to claim 1, wherein subjecting the product stream to the ion-exclusion chromatography comprises placing the product stream in contact with a resin in a sodium form.

* * * * *